US00PP08711P

United States Patent [19]

VandenBerg

[11] Patent Number: Plant 8,711

[45] Date of Patent: May 3, 1994

[54] CHRYSANTHEMUM PLANT NAMED RED CUMBIA

[75] Inventor: Cornelis P. VandenBerg, Salinas, Calif.

[73] Assignee: Yoder Brothers, Inc., Barberton, Ohio

[21] Appl. No.: 43,490

[22] Filed: Apr. 1, 1993

[51] Int. Cl.[5] ..... A01H 5/00

[52] U.S. Cl. ..... Plt./82.5

[58] Field of Search ..... Plt. 74.1, 82.5

[56] References Cited

U.S. PATENT DOCUMENTS 4,616,099 10/1986 Sparkes ..... 47/58

OTHER PUBLICATIONS

Chan, 1966, "Chrysanthemum and Rose Mutations Induced by X-Rays", Am. Soc. Hort. Sci. Proc., pp. 613-620.

Broertjes, 1966, "Mutation Breeding of Chrysanthemums", Euphytica, 15:156-162.

Dowrick, et al., 1966, "The Induction of Mutations in Chrysanthemum Using X- and Gamma Radiation", Euphytica, 15:204-210.

Broertjes, et al., 1980, "A Mutant of a Mutant of a . . . Irradiation of Progressive Radiation-Induced Mutants in a Mutation Breeding Programme with *Chrysanthemum morifolium*", Euphytica, 29:526-530.

Gosling, ed., 1979, The Chrysanthemum Manual-6th edition, The National Chrysanthemum Society, London, Essex Telephone Press, Ltd., pp. 329-336.

Broertjes, et al., 1978, "Application of Mutation Breeding Methods in the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

*Primary Examiner*—Howard J. Locker

*Attorney, Agent, or Firm*—Foley & Lardner

[57] ABSTRACT

A Chrysanthemum plant named Red Cumbia particularly characterized by its flat capitulum form; daisy capitulum type; dark red ray floret color; diameter across face of capitulum of 95 to 108 mm when fully opened, when grown as a single stem spray cut mum; photoperiodic flowering response to short days when grown in Salinas, Calif., is 52 to 56 days after start of short days; flowering response in Bogota, Colombia is 70 to 77 days; plant height is 84 to 104 cm when grown in Salinas with 3 to 11 long days prior to start of short days; height is 99 to 112 cm when grown in Bogota with 7 long days prior to start of short days; peduncle length of the first lateral at flowering after removing the apical bud and without growth regulator applications is 5 to 18 cm when grown in Salinas, and 15 to 18 cm when grown in Bogota; peduncle length of the fourth lateral at flowering is 13 to 23 cm when grown in Salinas, and 20 to 23 cm when grown in Bogota; many of the ray floret tips are double indented, with the cross section of the petal tips strongly convex; large, very attractive and deeply lobed and strongly serrated foliage; and excellent tolerance to low night temperatures for bud initiation and flower development.

1 Drawing Sheet

The present invention comprises a new and distinct cultivar of Chrysanthemum, botanically known as *Dendranthema grandiflora*, and referred to by the cultivar name Red Cumbia.

Red Cumbia, identified as 3500 (87-505E01), is a product of a mutation induction program. The new cultivar was discovered and selected by Cornelis P. VandenBerg on Nov. 28, 1990, in a controlled environment in Salinas, Calif., as one flowering plant within a flowering block established as rooted cuttings from stock plants which had been exposed as unrooted cuttings to an X-ray source of 2000 rads in Fort Myers, Fla., on May 31, 1990.

The irradiated parent cultivar was the cultivar identified as Cumbia, disclosed in U.S. Plant Pat. No. 8,113, and described as a spray cut mum with flat capitulum form; daisy capitulum type; dark red-purple ray floret color; diameter across face of capitulum of 95 to 108 mm when fully opened; flowering response period of 50 to 57 days after start of short days in Salinas, Calif., and 65 to 72 days in Bogota, Colombia; plant height of 89 to 119 cm when grown in Salinas with 3 to 11 long days prior to start of short days, and 107 to 132 cm when grown in Bogota with 7 to 17 long days prior to start of short days; and excellent tolerance to low night temperatures for bud initiation and flower development. The foregoing description of Cumbia has a somewhat wider range of measurements than the description of Cumbia in the noted plant patent. This is based on continued flowering trials of Cumbia after preparing and filling the patent application for Cumbia.

The irradiation program resulting in Red Cumbia had as its primary objective the expansion of ray floret color ranges of the parent cultivar Cumbia. The irradiation program comprised irradiating cuttings of the parent cultivar at irradiation levels of 1500, 1750 and 2000 rads. A total of 1539 cuttings harvested from a total of 225 irradiated plants were planted on Sep. 24, 1990, Sep. 17, 1990 and Sep. 17, 1990, respectively. Of these, 9 initial selections were made, which selections were then revegetated and reflowered. Three consecutive flowerings resulted in discarding 5 of the original 9 selections on Aug. 9, 1991, while 4 codes were retained as PI (Possible Introduction) status. The four retained codes were further tested in Salinas, Calif., and in Bogota, Colombia, ultimately resulting in the decision to discard three of the remaining selections on Apr. 26, 1992, and to introduce the one remaining selection as Red Cumbia.

The first act of asexual reproduction of Red Cumbia was accomplished when vegetative cuttings were taken from the original selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Red Cumbia are firmly fixed and are retained through successive generations of asexual reproduction.

Red Cumbia has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and in Bogota, Colombia, under greenhouse conditions which approximate those generally used in commercial greenhouse practice. The low night temperature tolerance was determined in repeated flowerings in Bogota, Colombia, at temperatures as low as 5°-10° C.

The following traits have been repeatedly observed and are determined to be basic characteristics of Red Cumbia, which, in combination, distinguish this Chrysanthemum as a new and distinct cultivar:

1. Flat capitulum form.
2. Daisy capitulum type.
3. Dark red ray floret color.
4. Diameter across face of capitulum of 95 to 108 mm when fully opened, when grown as a single stem spray cut mum.
5. Photoperiodic flowering response is 52 to 56 days after start of short days when grown in Salinas, Calif. Flowering response in Bogota, Colombia is 70 to 77 days.
6. Plant height is 84 to 104 cm when grown in Salinas with 3 to 11 long days prior to start of short days; height is 99 to 112 cm when grown in Bogota with 7 long days prior to start of short days.
7. Peduncle length of the first lateral at flowering after removing the apical bud and without growth regulator applications is 5 to 18 cm when grown in Salinas, and 15 to 18 cm when grown in Bogota. Peduncle length of the fourth lateral at flowering is 13 to 23 cm when grown in Salinas, and 20 to 23 cm when grown in Bogota.
8. Many of the ray floret tips are double indented, with the cross section of the petal tips being strongly convex.
9. Large, very attractive and deeply lobed and strongly serrated foliage.
10. Excellent tolerance to low night temperatures for bud initiation and flower development.

The accompanying color photographic drawing is a front view of a single stem cut spray mum of Red Cumbia, with the colors being as nearly true as possible with illustrations of this type.

Of the commercial cultivars known to the inventor, the most similar in comparison to Red Cumbia is the parent cultivar Cumbia. All traits of Red Cumbia are similar to those of Cumbia, except for the ray floret color, the flowering response and the plant height. The ray floret color of Red Cumbia is a dark red, while the ray floret color of Cumbia is described as a dark red-purple. In most of the flowering trials the response of Red Cumbia has been 2 to 4 days slower than the response of Cumbia, and Red Cumbia is 5 to 10 cm shorter than Cumbia when grown side by side.

In the following descrition color references are made to The Royal Horticultural Society Colour Chart. The actual color of the ray florets of Red Cumbia is not precisely represented in The RHS Colour Chart, and the values given are those believed to be closest to the actual color of Red Cumbia. The color values were determined on plant material grown as a single stem spray cut mum in Salinas, Calif. on Dec. 30, 1991.

Classification:

*Botanical.*—*Dendranthema grandiflora* cv Red Cumbia.

*Commercial.*—Flat daisy cut spray mum.

INFLORESCENCE

A. Capitulum:

*Form.*—Flat.

*Type.*—Daisy.

*Diameter across face.*—95 to 108 mm when fully opened.

B. Corolla of ray florets:

*Color (general tonality from a distance of three meters).*—Dark red.

*Color (upper surface).*—Between 47A and 185A, slightly tinged with 184A.

*Color (under surface).*—179B to 179C.

*Shape.*—Many tips of ray florets are double indented; base of ray florets are concave, outer ray florets are longitudinally convex, and cross section of tips of ray florets are strongly convex.

C. Corolla of disc florets:

*Color (mature).*—12A.

*Color (immature).*—12A, overlaid with 144B.

D. Reproductive organs:

*Androecium.*—Present on disc florets only; moderate pollen.

*Gynoecium.*—Present on both ray and disc florets.

PLANT

A. General appearance:

*Height.*—84 to 104 cm when grown in Salinas with 3 to 11 long days prior to start of short days; height is 99 to 112 cm when grown in Bogota with 7 long days prior to start of short days.

B. Foliage:

*Color (upper surface).*—147A.

*Color (under surface).*—147B.

I claim:

1. A new and distinct Chrysanthemum plant named Red Cumbia, as described and illustrated.

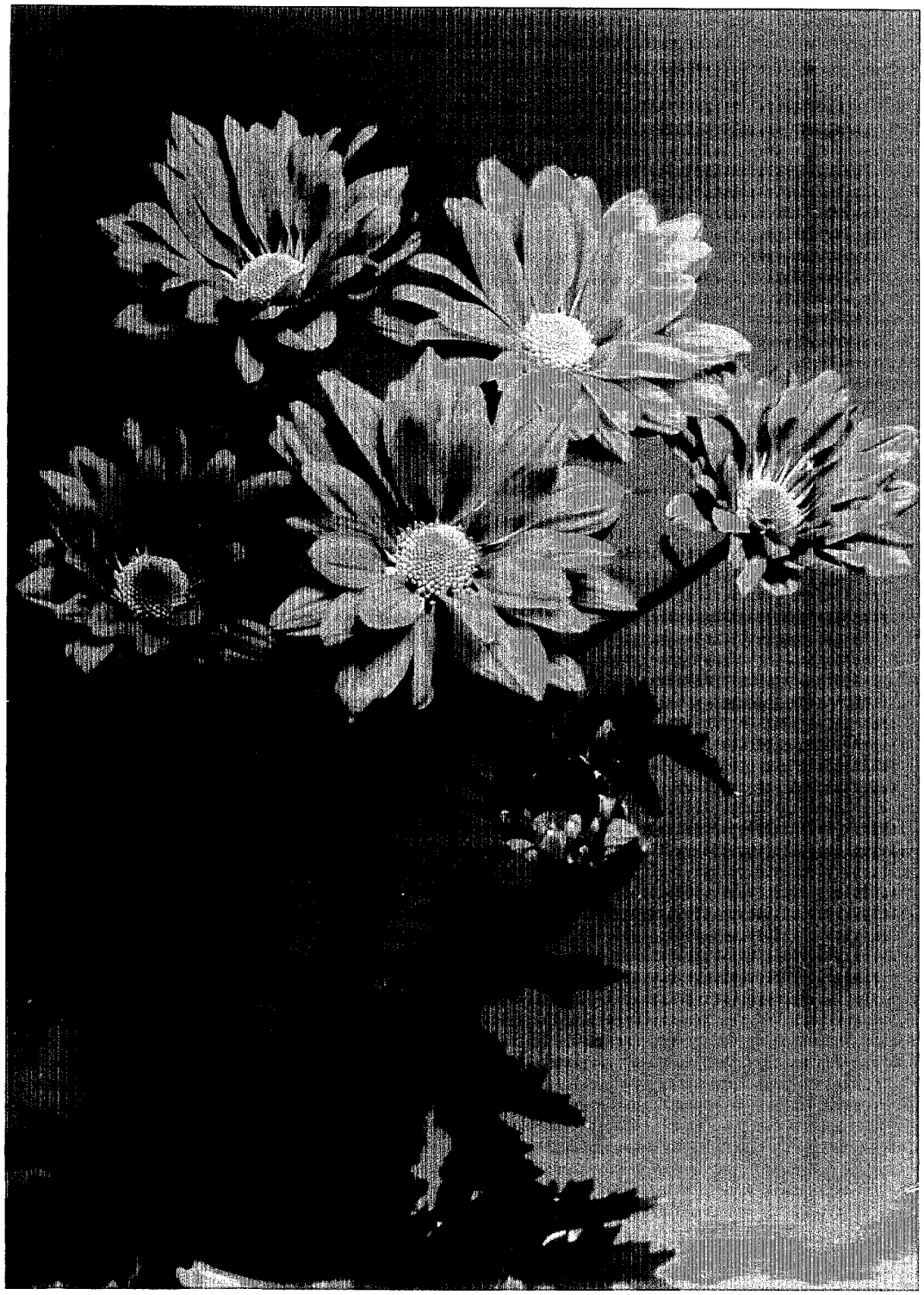

* * * * *